United States Patent
Kim et al.

(10) Patent No.: US 10,980,242 B2
(45) Date of Patent: *Apr. 20, 2021

(54) XYLARIA GRAMMICA EL 000614 STRAIN HAVING NEMATICIDAL ACTIVITY AGAINST ROOT KNOT NEMATODE AND USES THEREOF

(71) Applicants: INDUSTRY FOUNDATION OF CHONNAM NATIONAL UNIVERSITY, Gwangju (KR); NATIONAL INSTITUTE OF BIOLOGICAL RESOURCES, Incheon (KR)

(72) Inventors: Jin-Cheol Kim, Gwangju (KR); Tae Yoon Kim, Daegu (KR); Ja Yeong Jang, Jeollabuk-do (KR); Nan Hee Yu, Gwangju (KR); Won-Jae Chi, Gyeonggi-do (KR); Chang Hwan Bae, Gyeonggi-do (KR); Joo Hong Yeo, Gyeonggi-do (KR)

(73) Assignees: INDUSTRY FOUNDATION OF CHONNAM NATIONAL UNIVERSITY, Gwangju (KR); NATIONAL INSTITUTE OF BIOLOGICAL RESOURCES, Incheon (KR)

( * ) Notice: Subject to any disclaimer, the term of this patent is extended or adjusted under 35 U.S.C. 154(b) by 168 days.

This patent is subject to a terminal disclaimer.

(21) Appl. No.: 16/336,187

(22) PCT Filed: Sep. 27, 2017

(86) PCT No.: PCT/KR2017/010665
§ 371 (c)(1),
(2) Date: Mar. 25, 2019

(87) PCT Pub. No.: WO2018/062822
PCT Pub. Date: Apr. 5, 2018

(65) Prior Publication Data
US 2019/0223449 A1 Jul. 25, 2019

(30) Foreign Application Priority Data
Sep. 29, 2016 (KR) .................. 10-2016-0125511

(51) Int. Cl.
*A01N 63/30* (2020.01)
*C12R 1/645* (2006.01)
*C12N 1/14* (2006.01)
*A01N 25/26* (2006.01)
*A01N 25/14* (2006.01)

(52) U.S. Cl.
CPC ............ *A01N 63/30* (2020.01); *A01N 25/14* (2013.01); *A01N 25/26* (2013.01); *C12N 1/14* (2013.01); *C12R 1/645* (2013.01)

(58) Field of Classification Search
CPC ........ A01N 63/30; A01N 25/26; A01N 25/14; C12R 1/645; C12N 1/14
See application file for complete search history.

(56) References Cited

FOREIGN PATENT DOCUMENTS

| KR | 10-2003-0063955 A | 7/2003 |
|---|---|---|
| KR | 10-0574348 B1 | 4/2006 |
| KR | 10-2010-0116562 A | 11/2010 |
| KR | 10-2011-0087918 A | 8/2011 |
| KR | 10-1503916 B1 | 3/2015 |
| KR | 10-2016-0048375 A | 5/2016 |

OTHER PUBLICATIONS

Kim, T.Y., Jang, J.Y., Yu, N.H., Chi, W.J., Bae, C.H., Yeo, J.H., Park, A.R., Hur, J.S., Park, H.W., Park, J.Y. and Park, J.H., "Nematicidal activity of grammicin produced by Xylaria grammica KCTC 13121 BP against Meloidogyne incognita", Pest Management Science, 2018, 74(2), 384-391;published Aug. 29, 2017.*
International Search Report for PCT/KR2017/010665 dated Jan. 22, 2018.
Internet Webpage, Im, Jeong Ye, "Natural Material Substitutes for Pesticide found in Domestic Wild Mold", Monthly Cancer, Internet article, 2017, <URL: http://www.cancerline.co.kr/html/18000.html> (English machine translation is submitted herewith.).
Sung Min Hwang et al., "Occurrence of Meloidogyne incognita Infecting Resistant Cultivars and Development of an Efficient Screening Method for Resistant Tomato to the Mi-virulent Nematode", Korean journal of horticultural science and technology, vol. 32(2), pp. 217-226, 2014 (English translation of abstract is submitted herewith).
W.S.Abbott, "A method of Computing the Effectiveness of an Insecticide", Journal of the American Mosquito Control Association, Nol. 3 (2), 1987.

* cited by examiner

*Primary Examiner* — Mina Haghighatian
*Assistant Examiner* — Nathan W Schlientz
(74) *Attorney, Agent, or Firm* — The PL Law Group, PLLC

(57) ABSTRACT

*Xylaria grammica* EL 000614 strain has a nematicidal activity against root knot nematode. A method for controlling root knot nematode includes treating a crop, a crop seed, or a field for cultivation with a nematicidal microorganism formulation. The method has very little possibility of having a problem related to environmental contamination, and exhibits a high mortality and activity of inhibiting egg hatching for sweet potato root knot nematode (*M. incognita*). It is expected that the strain can be very advantageously used as an innovative biological control agent which enables prevention of problems associated with environmental contamination.

12 Claims, 6 Drawing Sheets
Specification includes a Sequence Listing.

XYLARIA GRAMMICA EL 000614 STRAIN HAVING NEMATICIDAL ACTIVITY AGAINST ROOT KNOT NEMATODE AND USES THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/010665, filed on Sep. 27, 2017, which claims priority to the benefit of Korean Patent Application No. 10-2016-0125511 filed in the Korean Intellectual Property Office on Sep. 29, 2016, the entire contents of which are incorporated herein by reference.

TECHNICAL FIELD

The present invention relates to *Xylaria grammica* EL 000614 strain having nematicidal activity against root knot nematode and uses thereof.

BACKGROUND ART

Plant parasitic nematodes feeding on nutrients after their invasion of plant root are known as a pathogen that attacks a crop. Production loss of representative 40 crops caused by nematode infection makes up 10% of the loss of the entire production amount of crops, and the damage cost tends to increase every year. As the plant parasitic nematodes causing a damage on crops all over the world, there is a root knot nematode as a representative example. The root knot nematode (*Meloidogyne* spp.) has a broad host range like infecting about 2,000 kinds of plants, and, while parasitizing inside a root of a plant, it completes its life cycle by feeding on nutrients from the plant. In accordance with an increase in cultivation in facilities, number of the root knot nematodes has also increased dramatically, thus causing rapid increase in damage to crops. As four kinds of the nematodes that are taken seriously in agriculture, there are sweet potato root knot nematode (*Meloidogyne incognita*), carrot root knot nematode (*Meloidogyne hapla*), Java root knot nematode (*Meloidogyne javanica*), and peanut root knot nematode (*Meloidogyne arenaria*). Among them, *Meloidogyne incognita* is particularly problematic in cultivation facilities in South Korea.

Meanwhile, as a conventional method for reducing or controlling a damage to crops caused by nematode infection, there are soil fuming, soil over-humidification, artificial increase of temperature inside a green house, crop rotation, or the like. However, as those methods exhibit an influence on crops and cannot control completely the nematodes, it cannot be said that they are a favorable method. Other than those, a method of using chemical pesticide has been developed, but it also has a problem like toxicity for human body and environment. Accordingly, to replace those methods, various studies are currently carried out. As a representative example of the study for controlling nematodes, there are studies as follows: 1) study of nematode control by using plant-derived resistant gene, 2) study using proteins and peptides which exhibit toxicity for nematodes, 3) study of nematode control by using a natural product or a plant metabolite, 4) study using nematode-repelling material and plant, 5) environment-friendly control method, and 6) study of nematode control using genetic information and protein information of nematodes. Accordingly, studies of selecting the strains with nematicidal activity by nematicidal activity screening for culture of various microorganisms and developing strains for controlling diseases that are caused by plant parasitic nematodes are continuously under progress.

Meanwhile, in Korean Patent Registration No. 0574348, "*Xylaria* sp. AH001 strain producing griseofulvin, formulation for controlling plant diseases containing same, and method for controlling plant diseases by using same" is disclosed, and in Korean Patent Application Publication No. 2010-0116562, "*Bacillus velezeneis* G341 strain and method for controlling plant disease using same" is disclosed. However, nothing has been described with regard to *Xylaria grammica* having nematicidal activity against root knot nematode as described in the present invention.

SUMMARY

The present invention is devised under the circumstances described above, and, according to the present invention, strains having nematicidal activity against root knot nematode were screened by using various microorganisms to develop an environment-friendly method for controlling plant parasitic nematodes. As a result, it was found that the culture filtrate of *Xylaria grammica* exhibits a very potent nematicidal activity. Furthermore, among the four strains of *Xylaria grammica*, the nematicidal activity of EL 000614 strain was the most excellent, in particular.

Thus, after examining the nematicidal activity against sweet potato root knot nematode (*Meloidogyne incognita*) and carrot root knot nematode (*Meloidogyne hapla*) as a main cause of root knot nematode disease by using, as a subject, various microorganisms separated from various natural environments of oversea countries as well as South Korea, it was able to confirm that microorganisms showing an excellent nematicidal activity can be provided. The present invention is completed accordingly.

To achieve the object described above, the present invention provides *Xylaria grammica* EL 000614 strain having nematicidal activity against root knot nematode.

Furthermore, the present invention provides a nematicidal microorganism formulation for root knot nematodes containing, as an effective ingredient, the aforementioned strain, a spore, a fungal hyphal mass, or a culture broth thereof.

Furthermore, the present invention provides a method for controlling root knot nematode comprising treating a crop, a crop seed, or a field for cultivation with the nematicidal microorganism formulation for root knot nematodes.

Still furthermore, the present invention provides a method for preparing a nematicidal microorganism formulation for root knot nematodes comprising culturing the aforementioned strain.

*Xylaria grammica* EL 000614 strain of the present invention for controlling nematodes is a strain isolated from lichen (*Usnea* sp.) that are found in rocks and trees of Mt. Jiri in South Korea. Because *Xylaria grammica* EL 000614 strain has very little possibility of having a problem related to environmental contamination as it has been collected from nature, and exhibits a high mortality and activity of inhibiting egg hatching for sweet potato root knot nematode (*M. incognita*) and also s high mortality against carrot root knot nematode (*M. hapla*), the strain of the present invention is expected to be very advantageously used as an innovative biological control agent which enables prevention of problems associated with environmental contamination.

DETAILED DESCRIPTION

Figure 1:
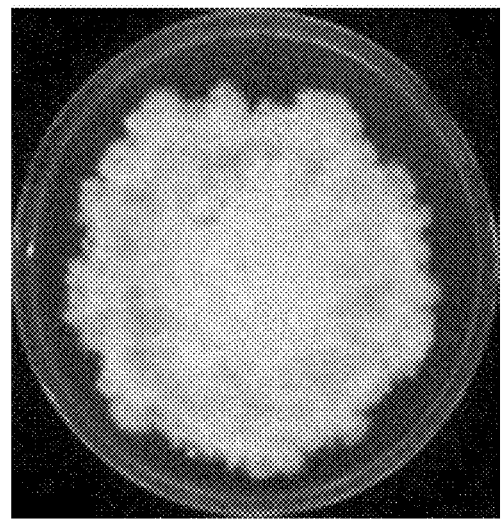
FIG. 1 is the result of naked eye observation of *Xylaria grammica* EL 000614 strain grown on PDA medium for 7 days.

To achieve the object described above, the present invention provides *Xylaria grammica* EL 000614 strain having nematicidal activity against root knot nematode.

According to the present invention, it is confirmed that the culture filtrate of *Xylaria* grammica EL 000614 strain exhibits the highest mortality and the highest effect of inhibiting egg hatching against root knot nematode (*Meloidogyne* sp.). *Xylaria* grammica EL 000614 strain was deposited in the Korea Research Institute of Bioscience and Biotechnology (having the address of 181, Ipsin-gil, Jeongeup-si, Jeollabuk-do 56212, Republic of Korea under the Access number of KCTC 13121BP on Sep. 28, 2016. The deposit has been made under the terms of the Budapest Treaty and all restrictions imposed by the depositor on the availability to the public of the biological material will be irrevocably removed upon the granting of a patent.

In the strain according to one exemplary embodiment of the present invention, the root knot nematode can be a strain of *Meloidogyne* sp., and it may be preferably *Meloidogyne incognita* or *Meloidogyne hapla*, but it is not limited thereto.

Furthermore, the present invention provides a nematicidal microorganism formulation for root knot nematodes containing, as an effective ingredient, the aforementioned strain, a spore, a fungal hyphal mass, or a culture broth thereof.

The microorganism formulation may contain *Xylaria grammica* EL 000614 strain having nematicidal activity against root knot nematode, or a spore, a fungal hyphal mass or a culture broth thereof as an effective ingredient.

Preferably, the microorganism formulation may be a suspension concentrate (SC), suspension microbial (SM), absorbent granule (absorbent GR), powdery granule (powdery GR) or wettable powder (WP) formulation, most preferably a wettable powder formulation, but it is not limited thereto.

The microorganism formulation contains a culture broth prepared by culturing the strain of the present invention, and thus may be used as a microbial pesticide, a seed coating agent, a microbial nutrient, a soil conditioning agent, a compost fertilizing agent, a foliar spray formulation, or a drench-spray formulation.

In the microorganism formulation of the present invention, *Xylaria grammica* EL 000614 strain or the culture broth thereof may be modified, as liquid and powdery phases, to various forms by known methods used in a related art. Preferably, a culture broth or concentrate of *Xylaria grammica* EL 000614 strain may be adsorbed onto a carrier such as starch, crude proteins, or stone powder, and then dried. The carrier that may be used as a mixture with the culture broth or concentrate of the strain of the present invention may include any carriers used in a related art. Specifically, the carrier that may be used in the present invention includes cereal such as rice, wheat, corn, barley, bean, millet, sorghum, millet, buckwheat, etc., tuber crops such as potato, etc., tuberous roots such as sweet potato, cassava, etc., or processed products thereof (for example, powder), starches derived therefrom, and derivatives thereof. In addition, agar, gelatin, pectate (polygalacturonate), chitosan, carboxymethyl cellulose and derivatives thereof, gelite, natural wax, natural gum, kaolin, clay minerals such as bentonite, or kieselguhr materials such as geolite may be used as the carrier. Such various carriers may be used alone, or two or more carriers may be mixed at a proper ratio to give a carrier having improved physical properties. When the aforementioned carriers are used, the carriers may be metabolized into nutrients by microorganisms, and may have an increased adhesive property to a surface of a plant due to their high viscosity, and thus favorable.

Also encompassed by the present invention is a dried product obtained by drying the strain or the strain culture broth, and a biological pesticide including the same. The dried product may be used as a formulation selected from the group consisting of a wettable powder (WP), a granular material (GM), a water-dispersible granule (WG), a granule (GR), a dustable powder (DP), and a water dispersible powder for seed treatment (WS) to prepare a biological pesticide. Such a biological pesticide formulation has excellent stability and physicochemical properties, compared to conventional liquid formulations, and may be used to control plant diseases.

Among the biological pesticides, the wettable powder refers to an agricultural pesticide formulation that is in a powdery phase but gets hydrated as soon as it is diluted with water, and the granular material refers to a formulation in which a culture broth of microorganisms is mixed with or adsorbed onto a solid material, that is, a formulation which does not belong to the granule or wettable powder formulations. Also, the water-dispersible granule refers to an agricultural pesticide formulation that is in a granular phase and used after being diluted with water, the granule refers to an agricultural pesticide formulation that is in a granular phase and used as it is, the dustable powder refers to an agricultural pesticide formulation that is in a powdery phase and used in the form of powder, and the water dispersible powders for seed treatment refers to an agricultural pesticide formulation that is in a powdery phase but hydrated for use as a suspension prior to treatment of seeds.

To control root knot nematodes by using the microorganism formulation of the present invention, the microorganism formulation may be homogeneously diluted using water, and then sprayed on a crop, a crop seed or a field using a suitable spraying device such as a motor sprayer. When the formulation of the present invention is diluted with water, concentration of the formulation may be adjusted to be in a range of $10^3$ to $10^5$ cfu/mL, preferably approximately $10^4$ cfu/mL so that the effective ingredient is within a biologically effective range, but it is not limited thereto.

Furthermore, the present invention provides a method for controlling root knot nematode (*Meloidogyne* sp.) comprising treating a crop, a crop seed, or a field for cultivation with the nematicidal microorganism formulation for root knot nematodes.

The method for controlling the root knot nematode (*Meloidogyne* sp.) may be carried out by dipping a crop or a crop seed in a culture broth obtained by culturing the strain of the present invention or a microorganism formulation using the strain, or by drenching, that is, spraying the culture broth or the microorganism formulation onto the crop or crop seed. In the case of the dipping method, the culture broth and formulation may be spread on soil around plants, or the seed may be soaked in the culture broth and formulation. Plants that may be applied to the method of the present invention are not particularly limited.

Still furthermore, the present invention provides a method for preparing a nematicidal microorganism formulation for root knot nematodes (*Meloidogyne* sp.) comprising culturing the aforementioned strain. Any methods known in the related art may be used as a method for culturing *Xylaria grammica* EL 000614 strain and a method for preparation of the microorganism formulation, and they are not particularly to specific methods.

In addition, the strain may be cultured in a malt extract broth (MEB) medium, a potato dextrose broth (PDB) medium, a Czapek Dox broth (CDB) medium, or a Sabouraud dextrose broth (SDB) medium, preferably a PDB medium, but it is not limited thereto. In the present invention, after the strain is cultured, an *M. incognita* juveniles suspension is treated with a culture broth at a concentration of 10%, and the nematicidal activities are examined after 3 days by using a 96-well microplate bioassay. As a result, the strain has the highest mortality, i.e., it exhibits 94% control activity in the PDB medium. As such, the PDB medium is selected as an optimal medium.

Hereinbelow, the present invention will be described in detail with reference to the examples. However, it should be understood that the following examples are given only for the purpose of exemplification and it is evident that the scope of the present invention is not limited to the following examples.

EXAMPLES

Example 1. Culture of *Xylaria grammica* EL 000614 Strain

1) Stationary Culture Using PDA Medium

One type of *Xylaria grammica* EL 000614 which has been isolated from rocks and tress of Mt. Jiri in South Korea and 3 types of *Xylaria grammica* EL 000590, EL 000603, and EL 000682 which has been separated from lichen of Mt. Great Snow in Taiwan were obtained from Korean Lichen and Allied Bioresources Center of Sunchon National University. The obtained strains were subjected to stationary culture for 7 days at 25° C. condition in potato dextrose agar (PDA) medium. *Xylaria grammica* EL 000614 strain cultured in PDA medium has white hypha, which turned into black color over time, and the color of the back surface of medium turned into orange color. In accordance with the growth, the strain showed a growth state in which it becomes completely adhered onto the surface of medium in accordance with the growth (FIG. 1).

2) Shaking Culture Using PDB Medium

Edges of the hypha of vigorously growing *Xylaria grammica* EL 000614 strain were cut to a size of about 0.5 mm by using a mes. Ten agar plugs containing hyphae inoculated to potato dextrose broth (PDB) medium (500 ml conical flask, 100 ml PDB medium), followed by shaking for 14 days at conditions of 25° C. and 150 rpm. The color of the medium was changed to white during incubation. After 14 days, the hypha was removed by using 4 layer gauze, and thus only the culture filtrate was obtained. The culture filtrate of EL 000614 strain belonging to *Xylaria* sp. was stored in a 4° C. refrigerator for nematicidal activity assay to be carried out later.

Example 2. Determination of Mortality of Culture Filtrate of EL 000614 Strain Belonging to *Xylaria* sp. Against $2^{nd}$ Stage Juveniles Mortality assay of above-obtained culture filtrate of EL 000614 strain belonging to *Xylaria* sp. for sweet potato root knot nematode (*M. incognita*) and carrot root knot nematode (*M. hapla*) was carried out as follows.

Eggs of sweet potato root knot nematode (*M. incognita*) were obtained from roots of tomato which has been artificially infected by sweet potato root knot nematode (*M incognita*) in a green house of environment-friendly agriculture center of Chonnam National University (Gwangju, South Korea). Specifically, roots of a tomato plant infected by sweet potato root knot nematode (*M. incognita*) were washed with tap water to remove foreign substances. Thereafter, the roots were cut into pieces to a size of 1 cm, and then added with a 0.5% sodium hyphochlorite solution followed by crushing for 1 minute. After the crushing, by using a sieve consisting of double sieves, i.e., 45 μm sieve and 25 μm sieve, the eggs were separated. Based on Baermann funnel method, hatched juveniles was separated from the separated eggs and used for the experiment (Hwang et al., Kor J Hort Sci Technol. 2014; 32: 217-226).

Eggs of carrot root knot nematode (*M. hapla*) were obtained from *ginseng* which has been infected by carrot root knot nematode (*M. hapla*) in Jinan (Chollabuk-Do, South Korea). The eggs were added to roots of a tomato, which has been cultivated for 4 weeks, to have infection. From the roots of a tomato infected by carrot root knot nematode (*M. hapla*), eggs of carrot root knot nematode (*M. hapla*) were obtained in the same manner as the method described above. Based on Baermann funnel method, hatched juveniles was separated from the separated eggs and used for the experiment (Hwang et al., Kor J Hort Sci Technol. 2014; 32: 217-226).

In order to examine the mortality against 2nd stage juveniles, suspension of 2nd stage juveniles was added to each well of a 96-well microplate. Next, a treatment with the culture filtrate to have concentration of 0.08% to 20% was carried out, while adjusting the final well volume to 100 μl. After the treatment with a test material, the 96-well plate was shaken for 30 seconds, and, after addition to a plastic container having relative humidity of 100%, it was kept at room temperature. 72 Hours after the treatment with a test material, mortality was determined under an optical inverted microscope by using the equation shown below. As for the mortality, the linear nematode showing no movement was taken as dead nematode, the nematode showing movement of flexible curve was taken as live nematode, and the mortality was examined using the following equation (Abbott, 1925. J Am Mosq Control Assoc. 1987; 3:302-303. PMID: 3333059). All the experiments were repeated in triplicate Mortality (%)=[Mortality percentage in treatment−
mortality percentage of negative control/(100−
mortality percentage in negative control)]×100

Figure 2:
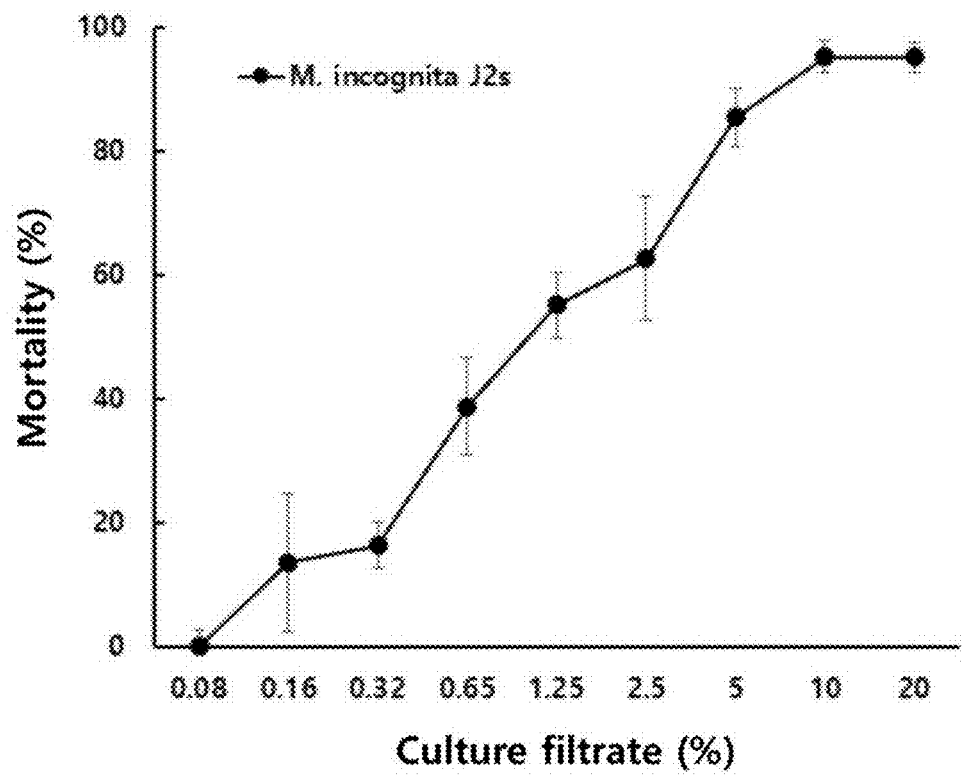
FIG. 2 shows the mortality of culture filtrate of *Xylaria grammica* EL 000614 strain against sweet potato root knot nematode (*M. incognita*), in which the culture filtrate has been obtained after stationary culture of *Xylaria grammica* EL 000614 strain on potato dextrose liquid medium for 14 days.

As a result, the mortality against sweet potato root knot nematode (*M. incognita*) was found to be dose-dependent as it is shown in FIG. 2. The mortality of 95% or higher was shown from the treatment group with 20% or 10% culture filtrate, and the mortality was 85.4% for 5% group, 62.7% for 2.5% group, 55.2% for 1.25% group, and 38.8% for 0.65% group, indicating the dose-dependent mortality.

Figure 3:
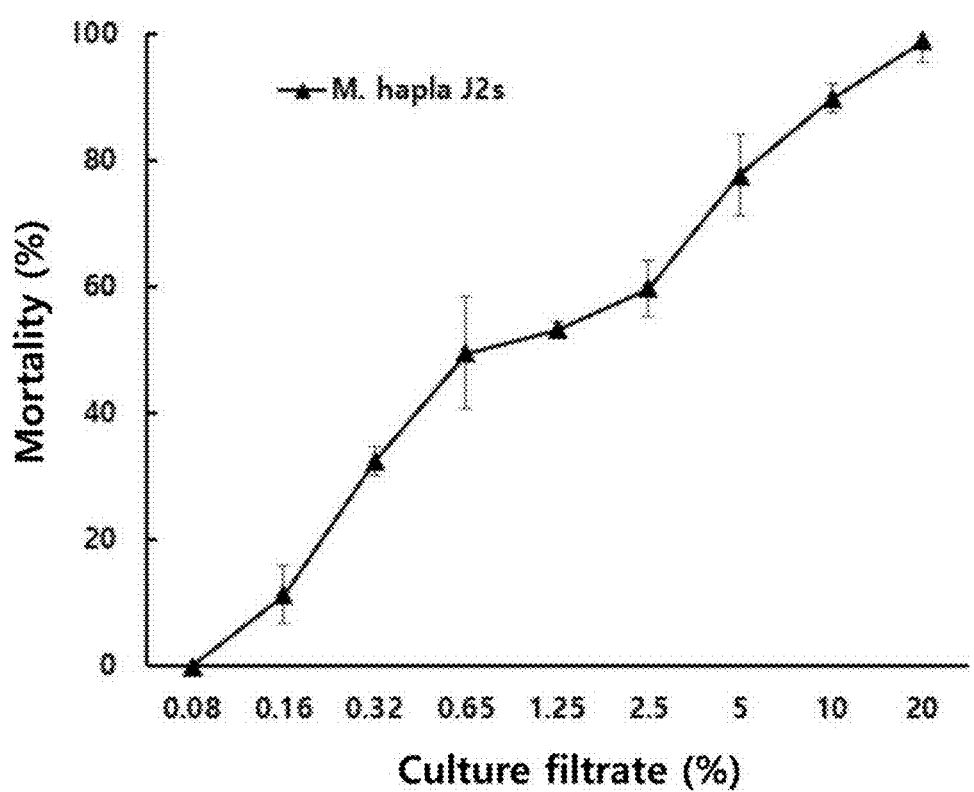
FIG. 3 shows the mortality of culture filtrate of *Xylaria grammica* EL 000614 strain against carrot root knot nematode (*M. hapla*), in which the culture filtrate has been obtained after stationary culture of *Xylaria grammica* EL 000614 strain on potato dextrose liquid medium for 14 days.

Also for the mortality against carrot root knot nematode (*M. hapla*), the mortality of 98.8% was shown from the 20% group, and it was 89.8% for 10% group, 77.6% for 5% group, 59.8% for 2.5% group, 53.2% for 1.25% group, and 49.5% for 0.65% group, as they are shown in FIG. 3.

As such, it was shown that the culture filtrate of *Xylaria grammica* EL 000614 exhibits a very high mortality not only against sweet potato root knot nematode (*M incognita*) but also against carrot root knot nematode (*M. hapla*).

Example 3. Molecular Biological Identification and Phylogenetic Analysis of Four Strains Belonging to *Xylaria* sp.

In order to have species-level identification of the four strains belonging to *Xylaria* sp., i.e., EL 000590, L 000603, EL 000614, and EL 000682, molecular biological identification and phylogenetic analysis were carried out therefor. The four strains were subjected to stationary culture in PDA medium. After that, cell bodies of each strain were collected, and, by using NucleoSpin Plant II kit of MACHEREY-NAGEL GMbH & CO. KG, genomic DNA (gDNA) was extracted according to the manufacturer's protocol. By mixing extracted gDNA of the strain, PCR-premix (Polymerase chain reaction-premix) of iNTRON Biotechnology, a primer set disclosed in the following Table 1 for amplifying an ITS (internal transcribed spacer) region of the strain, and deionized water, and carrying out PCR, the ITS region of the four strains was amplified. For the PCR, starting from 5 minutes at 95° C., a cycle of 30 seconds at 95° C., 30 seconds at 55° C., and 1 minute at 72° C. was repeated 30 times, and the amplification was terminated by 7 minutes at 72° C., and 12° C. The amplified PCR product was sent to Genotech (Daejon, South Korea) to have DNA sequencing, and thus nucleotide sequences of EL 000590 strain ITS (SEQ ID NO: 1), EL 000603 strain ITS (SEQ ID NO: 2), EL 000614 strain ITS (SEQ ID NO: 3), and EL 000682 strain ITS (SEQ ID NO: 4) were obtained. ITS nucleotide sequence of the four strains was compared to the nucleotide sequence of GenBank Database by using NCBI BlastN search (Table 2). In addition, based on the ITS nucleotide sequence of the *Xylaria* sp. strain, the nucleotide sequence was aligned by BioEdit Sequence Alignment Editorm. By using Mega Program version 6.0, phylogenetic analysis was carried out at conditions of boot-strap trials set 1,000 based on neighbor joining (NJ) algorithm.

Figure 4:
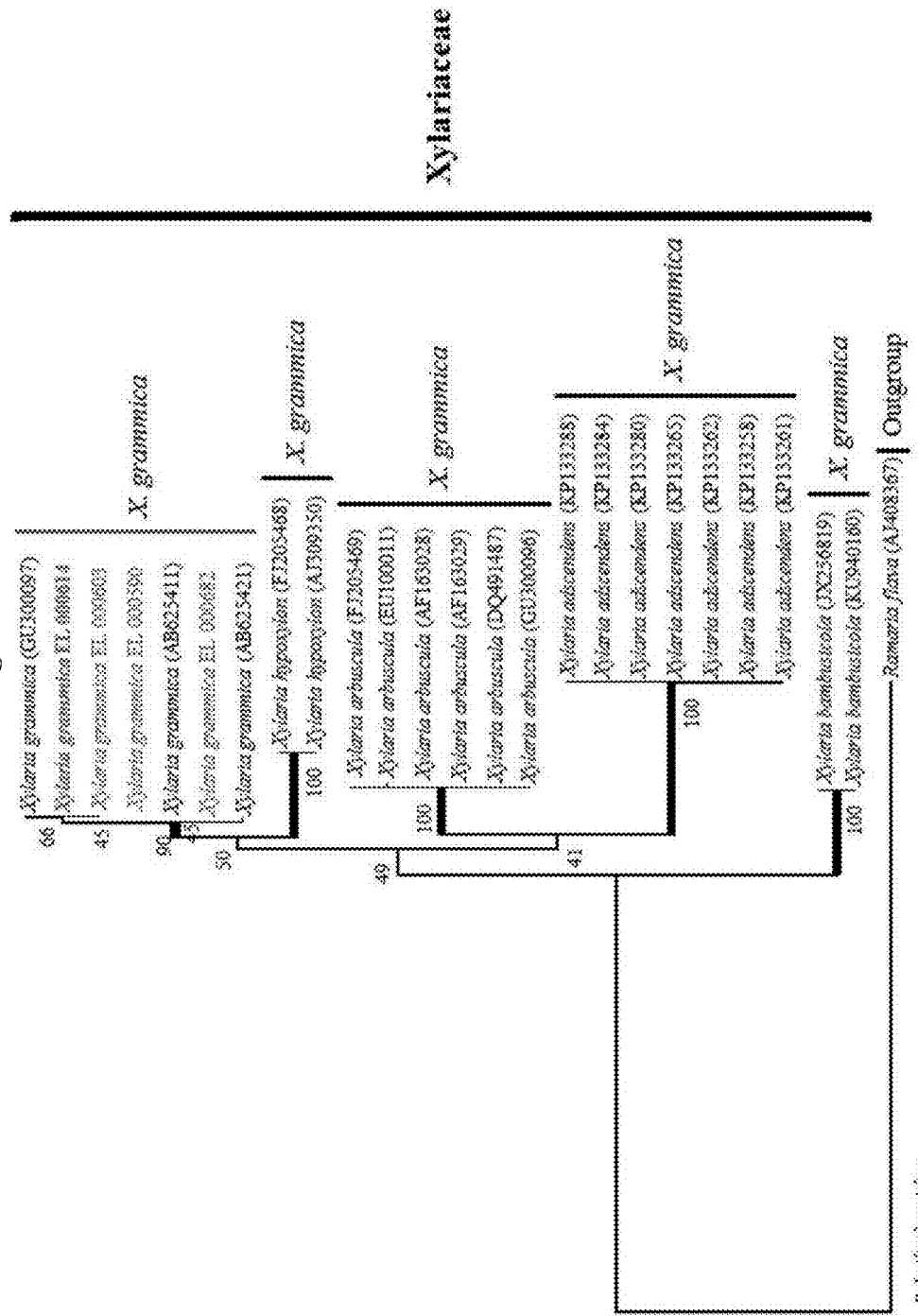
FIG. 4 is a tree diagram showing that, as a result of carrying out phylogenetic analysis based on nucleotide sequence analysis of ITS (internal transcribed spacer) of the four strains of *Xylaria* sp., all of the four strains are classified into *Xylaria grammica*.

As a result, all of the four strains were identified as a species of *Xylaria grammica*, and, among the strains obtained in the present invention, EL 000614 strain was named *Xylaria grammica* EL 000614 (FIG. 4) and deposited in the Korea Research Institute of Bioscience and Biotechnology on Sep. 28, 2016 to be given with Accession Number of KCTC 13121BP.

TABLE 1

Primers used in the present invention

| Gene for nucleotide sequencing | Primer name | SEQ ID NO: | Nucleotide sequence |
|---|---|---|---|
| ITS | ITS1F | 5 | 5'-TCC GTA GGT GAA CCT GCG G-3' |
|  | ITS4 | 6 | 5'-TCC TCC GCT TAT TGA TAT GC-3' |

TABLE 2

NCBI BlastN analysis result for ITS nucleotide sequence of four strains belonging to *Xylaria* sp.

| Gene for nucleotide sequencing | Strain number | Identification result based on NCBI BlastN analysis (GenBank accession no.) | Homology (%) |
|---|---|---|---|
| ITS | EL 000590 | *Xylaria grammica* (AB524025) | 99 |
|  | EL 000603 | *Xylaria grammica* (JQ341088) | 99 |
|  | EL 000614 | *Xylaria grammica* (AB524025) | 99 |
|  | EL 000682 | *Xylaria grammica* (JQ341088) | 99 |

Example 4. Determination of Mortality of Culture Filtrate Against Sweet Potato Root Knot Nematode (*M. incognita*) Depending on Culture Period of *Xylaria grammica* EL 000614 Strain and Selection of Optimum Strain To determine the mortality of the four *Xylaria grammica* strains depending on culture period, the culture was carried out for 7 days, 10 days, 14 days, or 21 days at the conditions that are described above. By filtering the cultured solution through 4 layer gauze, culture filtrate was obtained. In the same manner as Example 2, the mortality was determined for sweet potato root knot nematode (*M. incognita*), and all the experiments were carried out in triplicate.

Figure 5:
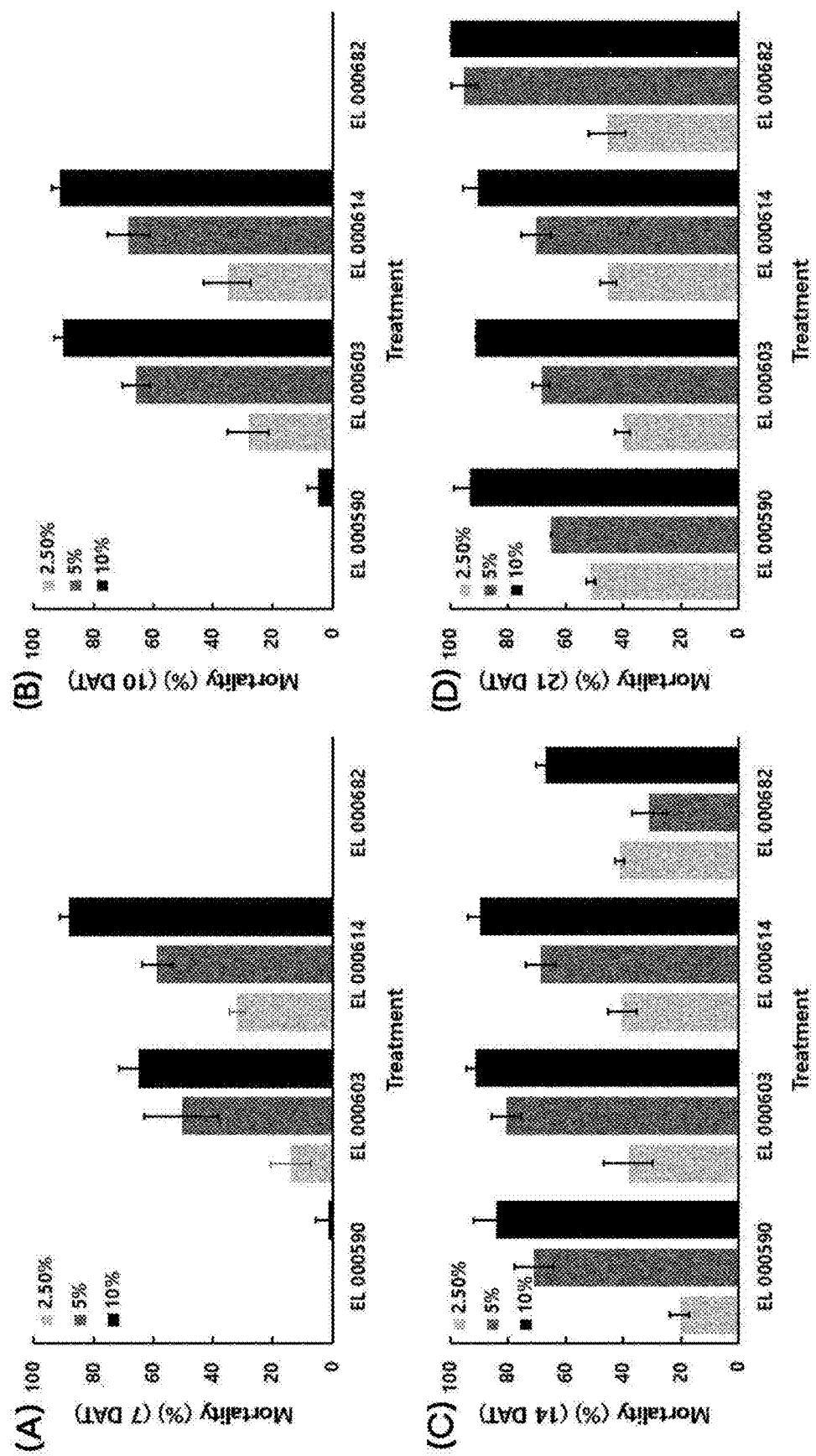
FIG. 5 shows the mortality of culture filtrate of the 4 strains of *Xylaria grammica* against 2nd stage juveniles of root knot nematode (*M. hapla*), in which the culture filtrate has been obtained after stationary culture of the 4 kinds of strain on potato dextrose liquid medium for 7 days, 10 days, 14 days, or 21 days; A: 7 days, B: 10 days, C: 14 days, and D: 21 days.

As a result, in case of *Xylaria grammica* EL 000614 among the four strains after the culture for 7 days, the mortality of 88.1% was shown from the 10% treatment group, 58.6% for 5% group, and 31.9% for 2.5% group, showing the highest activity, as shown in FIG. 5. In case of *Xylaria grammica* EL 000603 strain, the mortality of 65.5% was shown from the 10% treatment group, 50.5% for 5% group, and 14.1% for 2.5% group, while no activity was shown from *Xylaria grammica* EL 000590 and *Xylaria grammica* EL 000682. Results obtained after culture for 10 days were almost the same as the results obtained after culture for 7 days, showing the most excellent mortality from *Xylaria grammica* EL 000614, while no activity was shown from *Xylaria grammica* EL 000590 and *Xylaria grammica* EL 000682. 14 Days and 21 days after culture, the mortality was observed from all strains, but *Xylaria grammica* EL 000614 strain, which showed an excellent mortality within the shortest time period, was selected as an optimum strain.

Example 5. Activity of Inhibiting Egg Hatching of Sweet Potato Root Knot Nematode (*M. incognita*) by Culture Filtrate of *Xylaria grammica* EL 000614 Strain Activity of inhibiting egg hatching of sweet potato root knot nematode by culture filtrate of the selected *Xylaria grammica* EL 000614 strain was examined. The treatment concentration was from the minimum of 0.8% to the maximum of 20% of the culture filtrate. As a non-treatment group, PDB having no culture of any strain was used. As a control group, 0.5 μg/ml or 1 μg/ml abamectin was used. The experiments were carried out in triplicate, and the rate of inhibiting egg hatching was determined 14 days later. The rate of inhibiting egg hatching was calculated based on the following equation.

Rate of inhibiting egg hatching (%)=[(*C*−*T*)/*C*]×100,

C=Egg hatching rate of control*, T=Egg hatching rate of treatment
*Egg hatching rate (%)=Number of juveniles/[Number of eggs+Number of juveniles]×100

Figure 6:
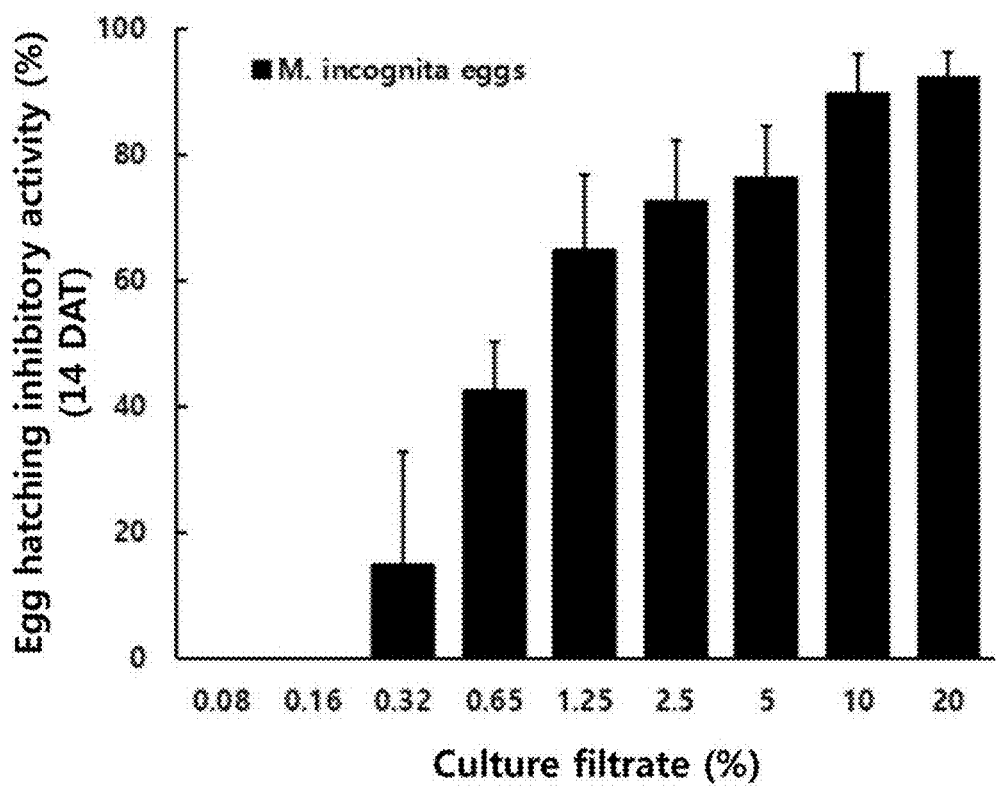
FIG. 6 shows the egg hatching inhibitory activity of the culture filtrate of *Xylaria grammica* EL 000614 strain against sweet potato root knot nematode (*M. incognita*), in which the culture filtrate has been obtained after stationary culture of *Xylaria grammica* EL 000614 strain on potato dextrose liquid medium for 14 days.

As a result, with regard to the rate of inhibiting egg hatching of sweet potato root knot nematode (*M. incognita*), it was shown that the activity of inhibiting egg hatching increases in accordance with an increase in the treatment concentration of cultured filtrate as it is illustrated in FIG. 6. The activity of inhibiting egg hatching was 92.1% from the 20% culture filtrate treatment group, while it was 89.5% from the 10% group, 76.3% from the 5% group, 72.5% from the 2.5% group, 64.8% from the 1.25% group, 42.6% from the 0.62% group, and 14.8% from the 0.32% group. It was shown that the culture filtrate of the selected *Xylaria grammica* EL 000614 strain not only has a high activity for 2nd stage juveniles of sweet potato root knot nematode (*M. incognita*) but also exhibits a high activity of inhibiting egg hatching.

Example 6. Determination of Mortality Depending on Method of Culturing Selected *Xylaria grammica* EL 000614 Strain In order to enhance the mortality of selected *Xylaria grammica* EL 000614 strain, the culture condition was modified, i.e., from shaking culture to stationary culture, for culturing *Xylaria grammica* EL 000614 strain. In case of the stationary culture for the strain, stationary culture was carried out for 14 days at 25° C. conditions in PDB medium, and in case of the shaking culture for the strain, shaking culture was carried out for 14 days at 25° C., 150 rpm conditions in PDB medium.

Figure 7:
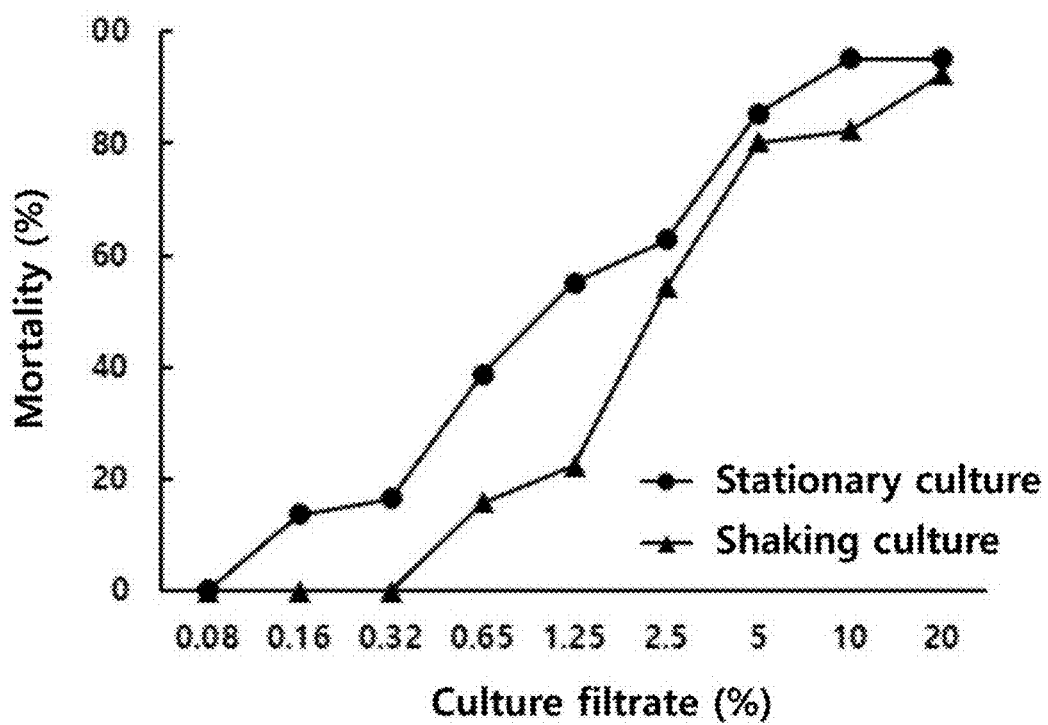
FIG. 7 shows the mortality of the culture filtrate of *Xylaria grammica* EL 000614 strain against 2 stage juveniles of sweet potato root knot nematode (*M. incognita*), in which the culture filtrate has been obtained after shaking culture or stationary culture of *Xylaria grammica* EL 000614 strain on potato dextrose liquid medium for 14 days.

As a result, the mortality was higher in the culture filtrate of the *Xylaria grammica* strain EL 000614 obtained after stationary culture compared to the mortality of the culture filtrate of the *Xylaria grammica* strain EL 000614 obtained after shaking culture, as it is shown in FIG. 7.

More specifically, the mortality of the culture filtrate obtained after shaking culture was 95.2% from the 20% group, while it was 89.8% from the 10% group, 68.8% from the 5% group, and 40.3% from the 2.5% group. On the other hand, the mortality of the culture filtrate obtained after stationary culture was 95.2% from the 20% group, while it was 90.0% from the 10% group, 72.3% from the 5% group, and 52.9% from the 2.5% group, thus showing a difference of about 10% in the mortality between the treatment group treated with 5% culture filtrate and the treatment group treated with 2.5% cultured filtrate.

The invention claimed is:

1. A method for controlling root knot nematode belonging to *Meloidogyne* sp., the method comprising:
preparing a nematicidal microorganism formulation comprising *Xylaria* grammica EL 000614 strain with at least 0.16% culture filtrate; and
treating a crop, a crop seed, or a field for cultivation with the nematicidal microorganism formulation comprising *Xylaria* grammica EL 000614 strain.

2. The method of claim 1, wherein the *Xylaria* grammica EL 000614 strain is the strain deposited with Korea Research Institute of Bioscience and Biotechnology under the accession number of KCTC 13121BP.

3. The method of claim 1, wherein the root knot nematode is *Meloidogyne incognita* or *Meloidogyne hapla*.

4. The method of claim 1, wherein the nematicidal microorganism formulation contains a spore of the *Xylaria* grammica EL 000614 strain.

5. The method of claim 1, wherein the nematicidal microorganism formulation contains a fungal hyphal mass of the *Xylaria* grammica EL 000614 strain.

6. The method of claim 1, wherein the nematicidal microorganism formulation contains a culture broth of the *Xylaria* grammica EL 000614 strain.

7. The method of claim 1, wherein the nematicidal microorganism formulation comprises a suspension concentrate, a suspension microbial, an absorbent granule, a powdery granule or a wettable powder (WP) formulation having the *Xylaria* grammica EL 000614 strain.

8. The method of claim 1, wherein the microorganism formulation comprises a culture broth prepared by culturing the *Xylaria* grammica EL 000614 strain, and the microorganism formulation is a seed coating agent, a microbial nutrient, a soil conditioning agent, a compost fertilizing agent, a foliar spray formulation, or a drench-spray formulation.

9. The method of claim 1, wherein the preparation of the nematicidal microorganism formulation comprises:
preparing a culture broth or a concentrate of the *Xylaria* grammica EL 000614 strain;
adsorbing the prepared culture broth or concentrate onto a carrier and drying the adsorbed culture broth or concentrate.

10. The method of claim 9, wherein the carrier is selected from the group consisting of cereal, a tuber crop, a tuberous root, and a combination thereof.

11. The method of claim 1, wherein the nematicidal microorganism formulation is a dried formulation selected from the group consisting of a wettable powder (WP), a granular material (GM), a water-dispersible granule (WG), a granule (GR), a dustable powder (DP), and a water dispersible powder for seed treatment (WS).

12. The method of claim 1, wherein a concentration of the nematicidal microorganism formulation is in a range of $10^3$ to $10^5$ cfu/mL.

* * * * *

SEQUENCE LISTING

```
<160> NUMBER OF SEQ ID NOS: 6

<210> SEQ ID NO 1
<211> LENGTH: 582
<212> TYPE: DNA
<213> ORGANISM: Xylaria grammica

<400> SEQUENCE: 1
gtaacaaggt ctccgttggt gaaccagcgg agggatcatt aaagagttat tacaactccc      60
aaacccatgt gaacttacct tctgttgcct cggcaggtcg cgacctaccc tgtgaggccc     120
taccctgtag ggccctacct ggtagtcgcg ggttacgcct gccggtggcc catgaaactc     180
tgtttattct tgttattctg aatctataac taaataagtt aaaactttca acaacggatc     240
tcttggttct ggcatcgatg aagaacgcag cgaaatgcga taagtaatgt gaattgcaga     300
attcagtgaa tcatcgaatc tttgaacgca cattgcgccc attagtattc tagtgggcat     360
gcctgttcga gcgtcatttc aacccttaag ccctgttgc ttagcgttgg gagcctacag      420
ccttctgtag ctccccaaag ttagtggcgg agtcggttta cactctagac gtagtaaatt     480
ttatctcgtc tgcagttagg ccggtccctc gccgtaaaac cccccaattt ttaaaggttg     540
acctcggatc aggtaggaat acccgctgaa cttaagcata tc                         582

<210> SEQ ID NO 2
<211> LENGTH: 581
<212> TYPE: DNA
<213> ORGANISM: Xylaria grammica
```

-continued

<400> SEQUENCE: 2

```
gtaacaaggt ctccgttggt gaaccagcgg agggatcatt aaagagttat tacaactccc    60
aaacccatgt gaacttacct tctgttgcct cggcaggtcg cgacctaccc tgtgaggccc   120
taccctgtag ggccctacct ggtagtcgcg ggtacgcctg ccggtggccc atgaaactct   180
gtttattctt gttattctga atctataact aaataagtta aaactttcaa caacggatct   240
cttggttctg gcatcgatga agaacgcagc gaaatgcgat aagtaatgtg aattgcagaa   300
ttcagtgaat catcgaatct ttgaacgcac attgcgccca ttagtattct agtgggcatg   360
cctgttcgag cgtcatttca acccttaagc ctctgttgct tagcgttggg agcctacagc   420
cttctgtagc tccccaaagt tagtggcgga gtcggtttac actctagacg tagtaaattt   480
tatctcgtct gcagttaggc cggtccctcg ccgtaaaacc ccctaatttt taaaggttga   540
cctcggatca ggtaggaata cccgctgaac ttaagcatat c                      581
```

<210> SEQ ID NO 3
<211> LENGTH: 581
<212> TYPE: DNA
<213> ORGANISM: Xylaria grammica

<400> SEQUENCE: 3

```
gtaacaaggt ctccgttggt gaaccagcgg agggatcatt aaagagttat tacaactccc    60
aaacccatgt gaacttacct tctgttgcct cggcaggtcg cgacctaccc tgtgaggccc   120
taccctgtag ggccctacct ggtagtcgcg ggtacgcctg ccggtggccc atgaaactct   180
gtttattctt gttattctga atctataact aaataagtta aaactttcaa caacggatct   240
cttggttctg gcatcgatga agaacgcagc gaaatgcgat aagtaatgtg aattgcagaa   300
ttcagtgaat catcgaatct ttgaacgcac attgcgccca ttagtattct agtgggcatg   360
cctgttcgag cgtcatttca acccttaagc ctctgttgct tagcgttggg agcctacagc   420
cttctgtagc tccccaaagt tagtggcgga gtcggtttac actctagacg tagtaaattt   480
tatctcgtct gcagttaggc cggtccctcg ccgtaaaacc cccaattttt taaaggttga   540
cctcggatca ggtaggaata cccgctgaac ttaagcatat c                      581
```

<210> SEQ ID NO 4
<211> LENGTH: 582
<212> TYPE: DNA
<213> ORGANISM: Xylaria grammica

<400> SEQUENCE: 4

```
gtaacaaggt ctccgttggt gaaccagcgg agggatcatt aaagagttat tacaactccc    60
aaacccatgt gaacttacct tctgttgcct cggcaggtcg cgacctaccc tgtgaggccc   120
taccctgtag ggccctacct ggtagtcgcg ggttacgcct gccggtggcc catgaaactc   180
tgtttattct tgttattctg aatctataac taaataagtt aaaactttca acaacggatc   240
tcttggttct ggcatcgatg aagaacgcag cgaaatgcga taagtaatgt gaattgcaga   300
attcagtgaa tcatcgaatc tttgaacgca cattgcgccc attagtattc tagtgggcat   360
gcctgttcga gcgtcatttc aacccttaag ccctgttgc ttagcgttgg gagcctacag   420
ccttctgtag ctccccaaag ttagtggcgg agtcggttta cactctagac gtagtaaatt   480
ttatctcgtc tgcagttagg ccggtccctc gccgtaaaac ccccaatttt taaaggttg   540
acctcggatc aggtaggaat acccgctgaa cttaagcata tc                     582
```

```
<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
tccgtaggtg aacctgcgg                                                19

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
tcctccgctt attgatatgc                                               20
```